United States Patent
Ippen et al.

Patent Number: 5,104,879
Date of Patent: Apr. 14, 1992

[54] ANTIMYCOTICALLY ACTIVE SUBSTITUTED 2-AMINOTHIAZOLES

[75] Inventors: Joachim Ippen; Bernd Baasner, both of Leverkusen; Klaus Schaller, Wuppertal; Miklos von Bittera, Leverkusen, all of Fed. Rep. of Germany

[73] Assignee: Bayer Aktiengesellschaft, Leverkusen, Fed. Rep. of Germany

[21] Appl. No.: 596,626

[22] Filed: Oct. 11, 1990

Related U.S. Application Data

[63] Continuation of Ser. No. 414,055, Sep. 28, 1989, abandoned.

Foreign Application Priority Data

Oct. 24, 1988 [DE] Fed. Rep. of Germany ....... 3836184

[51] Int. Cl.$^5$ .................. C07D 417/00; A01N 43/78
[52] U.S. Cl. .................................. 511/272; 544/331
[58] Field of Search ..................... 544/331; 514/272

[56] References Cited

U.S. PATENT DOCUMENTS 4,581,453 4/1986 Ippen ................... 544/331

FOREIGN PATENT DOCUMENTS 0095640 12/1983 European Pat. Off. .
2042315 2/1971 France .

*Primary Examiner*—Robert Gerstl
*Attorney, Agent, or Firm*—Sprung Horn Kramer & Woods

[57] ABSTRACT

Antimicotically active 2-aminothiazoles have been found having the formula

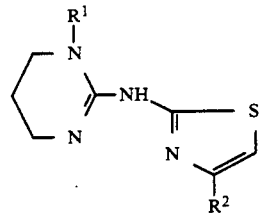

in which
$R^1$ represents hydrogen or alkyl and
$R^2$ represents optionally substituted cyclohexyl or phenyl which is substituted by halogen, alkyl, halogenoalkyl, halogenoalkoxy, dioxyhalogenoalkyl or halogenoalkylthio, and their physiologically tolerable acid addition salts, with the exception of the compounds 4-(4-chlorophenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and with the exception of the physiologically tolerable acid addition salts of these compounds have been found.

5 Claims, No Drawings

ANTIMYCOTICALLY ACTIVE SUBSTITUTED 2-AMINOTHIAZOLES

This application is a continuation of application Ser. No. 414,055, filed Sept. 28, 1989, now abandoned.

The invention relates to new substituted 2-aminothiazoles, a process for their preparation and their use in combating diseases, in particular mycoses.

It has been disclosed that certain substituted aminothiazoles, such as, for example, the compound 4-(2,4-dichlorophenyl)-2-[2-(1,4,5,6-tetrahydropyrimidinyl)-amino]-thiazole hydrochloride or the compound 4-(4-chloro-2-methylphenyl)-2-[2-(1,4,5,6-tetrahydropyrimidinyl)-amino]-thiazole hydrochloride or the compound 4-(4-chloro-2-methoxyphenyl)-2-[2-(1,4,5,6-tetrahydropyrimidinyl)-amino]-thiazole possess good antimycotic properties (compare, for example, German Offenlegungsschrift 3,220,118).

However, the activity of these known compounds is not completely satisfactory in all indications.

New substituted 2-aminothiazoles of the general formula (I)

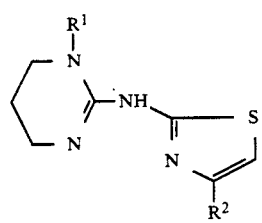

(I)

in which
$R^1$ represents hydrogen or alkyl and
$R^2$ represents optionally substituted cyclohexyl or phenyl which is substituted by halogen, alkyl, halogenoalkyl, halogenoalkoxy, dioxyhalogenoalkyl or halogenoalkylthio,
and their physiologically tolerable acid addition salts, with the exception of the compounds 4-(4-chlorophenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and with the exception of the physiologically tolerable acid addition salts of these compounds
have been found.

The compounds of the formula (I) are in equilibrium with the tautomeric compounds of the formulae (Ia) and (Ib)

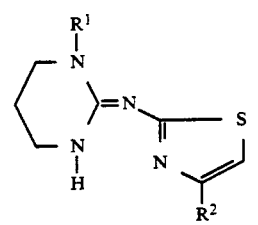

(Ia)

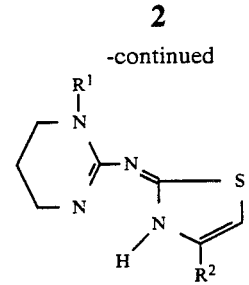

(Ib)

(where $R^1$ and $R^2$ in each case have the abovementioned meaning), and their use is likewise claimed according to the invention.

Furthermore, it has been found that the new substituted 2-aminothiazoles of the general formula (I)

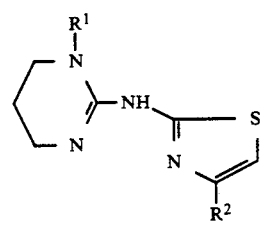

(I)

in which
$R^1$ represents hydrogen or alkyl and
$R^2$ represents optionally substituted cyclohexyl or phenyl which is substituted by halogen, alkyl, halogenoalkyl, halogenoalkoxy, dioxyhalogenoalkyl or halogenoalkylthio,
and their physiologically tolerable acid addition salts, with the exception of the compounds 4-(4-chloro-2-methoxyphenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and also with the exception of physiologically tolerable acid addition salts of these compounds
are obtained when thiourea derivatives of the formula (II)

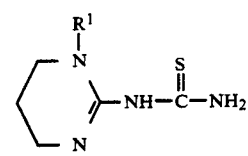

(II)

in which
$R^1$ has the abovementioned meaning,
are reacted with ketone derivatives of the formula (III)

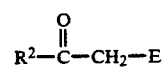

(III)

in which
$R^2$ has the abovementioned meaning and
E represents hydroxy or halogen,
if appropriate in the presence of a diluent and if appropriate in the presence of a reaction auxiliary and, if desired, an acid is then added.

Finally, it has been found that the new substituted 2-aminothiazoles of the general formula (I) possess good antimicrobial, in particular good antimycotic, properties.

Surprisingly, the substituted 2-aminothiazoles of the general formula (I) according to the invention show a considerably better antimycotic activity in certain indications than the substituted aminothiazoles known from the prior art, such as, for example, the compound 4-(2,4-dichlorophenyl)-2-[2-(1,4,5,6-tetrahydropyrimidinyl)-amino]-thiazole hydrochloride or the compound 4-(4-chloro-2-methylphenyl)-2-[2-(1,4,5,6-tetrahydropyrimidinyl)-amino]-thiazole hydrochloride or the compound 4-(4-chloro-2-methoxyphenyl)-2-[2-(1,4,5,6-tetrahydropyrimidinyl)-amino]-thiazole, which are closely related compounds chemically and with respect to their action.

Formula (I) provides a general definition of the substituted 2-aminothiazoles according to the invention.

Preferred compounds of the formula (I) are those in which $R^1$ represents hydrogen or straight-chain or branched alkyl having 1 to 4 carbon atoms and $R^2$ represents cyclohexyl which is optionally monosubstituted or polysubstituted by identical or different substituents, suitable substituents being: halogen, in particular fluorine, chlorine or bromine, in each case straight-chain or branched alkyl or alkoxy each having 1 to 4 carbon atoms or in each case straight-chain or branched halogenoalkyl or halogenoalkoxy each having 1 to 4 carbon atoms and 1 to 9 identical or different halogen atoms or represents phenyl which is monosubstituted or polysubstituted by identical or different substituents, suitable substituents being: halogen, in particular fluorine, chlorine or bromine, straight-chain or branched alkyl having 1 to 6 carbon atoms and also in each case straight-chain or branched halogenoalkyl,halogenoalkoxy,dioxyhalogenoalkylene or halogenoalkylthio each having 1 to 4 carbon atoms and 1 to 9 identical or different halogen atoms, in particular fluorine, chlorine or bromine, with the exception of the compounds 4-(4-chloro-2-methoxyphenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and with the exception of the physiologically tolerable acid addition salts of these compounds.

Particularly preferred compounds of the formula (I) are those in which $R^1$ represents hydrogen or methyl and $R^2$ represents cyclohexyl which is optionally monosubstituted to pentasubstituted by identical or different substituents from the series comprising methyl or ethyl or represents phenyl which is monosubstituted to pentasubstituted by identical or different substituents, suitable substituents being: fluorine, chlorine, bromine, straight-chain or branched alkyl having 1 to 4 carbon atoms or in each case straight-chain or branched halogenoalkyl, halogenoalkoxy, dioxyhalogenoalkylene or halogenoalkylthio each having 1 to 3 carbon atoms and 1 to 7 identical or different halogen atoms, in particular fluorine or chlorine, with the exception of the compounds 4-(4-chloro-2-methoxyphenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and also with the exception of the physiologically tolerable acid addition salts of these compounds.

Preferred compounds according to the invention are also addition products of acids and those substituted 2-aminothiazoles of the formula (I) in which the substituents $R^1$ and $R^2$ have the meanings which have already been mentioned as preferred for these substituents.

The acids which can be added preferably include hydrohalic acids, such as, for example, hydrochloric acid and hydrobromic acid, in particular hydrochloric acid, and in addition phosphoric acid, nitric acid, sulphuric acid, mono-, bi- and trifunctional carboxylic acids and hydroxycarboxylic acids, such as, for example, acetic acid, maleic acid, succinic acid, fumaric acid, glutaric acid, hydroxyglutaric acid, adipic acid, oleic acid, malonic acid, oxalic acid, tartaric acid, malic acid, citric acid, benzoic acid, salicylic acid, sorbic acid and lactic acid, sulphonic acids, such as, for example, methanesulphonic acid, p-chlorobenzenesulphonic acid, p-toluenesulphonic acid and 1,5-naphthalinedisulphonic acid, sulphuric acid half esters such as methyl hydrogen sulphate or ethyl hydrogen sulphate and also saccharin or thiosaccharin.

Very particularly preferred compounds of the formula (I) are those in which $R^1$ represents hydrogen, $R^2$ represents cyclohexyl which is monosubstituted, disubstituted or trisubstituted by methyl, or phenyl which is monosubstituted to pentasubstituted by identical or different substituents from the series comprising fluorine, chlorine, methyl, ethyl, trifluoromethyl, trifluoromethoxy, trifluoromethylthio, dioxydifluoromethylene or dioxytetrafluoroethylene, with the exception of the compounds 4-(4-chloro-2-methoxyphenyl)-2-[2-(1,4,5,6-tetrahydropyrimidinyl)-amino]-thiazole and 4-(2,4-dichlorophenyl)-2-[2-(1,4,5,6-tetrahydropyrimidinyl)-amino]-thiazole and 4-(4-chloro-2-methylphenyl)-2-[2-(1,4,5,6-tetrahydropyrimidinyl)-amino]-thiazole and also with the exception of the physiologically tolerable acid addition salts of these compounds.

If, for example, N-(1,4,5,6-tetrahydro-2-pyrimidinyl)-thiourea and ω-hydroxy-3-trifluoromethylacetophenone are used as starting substances, the course of the reaction of the preparation process can be represented by the following equation:

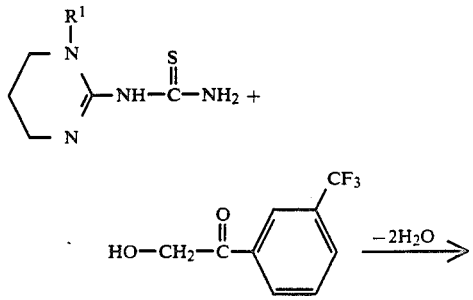

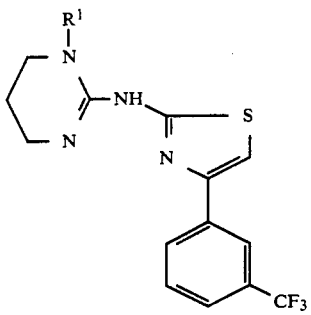

Formula (II) provides a general definition of the thiourea derivatives required as starting substances for carrying out the process according to the invention. In this formula (II), $R^1$ preferably represents those radicals which have already been mentioned as preferred for these substituents in connection with the description of the substances of the formula (I) according to the invention.

The thiourea derivatives of the formula (II) are known (compare, for example, Arzneim.-Forsch. 35, 573-577 [1985] or German Offenlegungsschrift 3,220,118 or EP-A-95,640) or obtainable in analogy to known processes (compare, for example, Organic Syntheses. Coll. Vol. IV, 502) for example when tetrahydropyrimidinylcyanamides of the formula (IV)

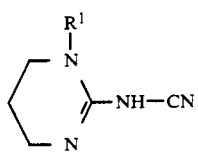

in which
$R^1$ has the abovementioned meaning,
are reacted with hydrogen sulphide, if appropriate in the presence of a diluent such as, for example, water and if appropriate in the presence of a reaction auxiliary such as, for example, sodium hydroxide, at temperatures between 20° C. and 120° C.

Tetrahydropyrimidinylcyanamides of the formula (IV) are known (compare, for example, German Offenlegungsschrift 2,205,745; German Offenlegungsschrift 2,205,744; J. Org. Chem. 38, 155-156 [1973]).

Formula (III) provides a general definition of the ketone derivatives furthermore required as starting substances for carrying out the process according to the invention. In this formula (III), $R^2$ preferably represents those radicals which have already been mentioned as preferred for these substituents in connection with the description of the substances of the formula (I) according to the invention. E preferably represents hydroxyl, chlorine or bromine.

The ketone derivatives of the formula (III) are known in some cases or can be obtained in analogy to generally known processes (compare, for example, German Offenlegungsschrift 2,445,120; U.S. Pat. No. 3,763,148; U.S. Pat. No. 3,753,997 or Org. Mass. Spectrom. 18, 601-607 [1983]).

New ketone derivatives of the general formula (III) are those of the formula (IIIa)

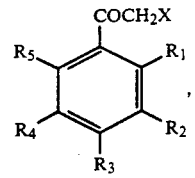

in which
X represents hydrogen, chlorine or bromine and the radicals $R_1$ to $R_5$ have the following meaning,
a) $R_1$ and $R_4$ denote fluorine, $R_2$ and $R_5$ denote chlorine and $R_3$ denotes $CF_3$ or
b) $R_1$, $R_3$ and $R_4$ denote fluorine, and $R_2$ and $R_5$ denote hydrogen or
c) $R_1$, $R_4$ and $R_5$ denote hydrogen, $R_2$ denotes chlorine and $R_3$ denotes $CF_3$ or
d) $R_1$, $R_4$ and $R_5$ denote hydrogen, $R_2$ denotes chlorine and $R_3$ denotes $OCF_3$ or
e) $R_1$, $R_4$ and $R_5$ denote hydrogen and $R_2$ and $R_3$ denote $CF_3$ or
f) $R_1$ denotes chlorine, $R_2$ denotes $CF_3$ and $R_3$, $R_4$ and $R_5$ denote hydrogen or
g) $R_1$ denotes chlorine, $R_2$, $R_3$ and $R_4$ denote hydrogen and $R_5$ denotes $CF_3$ or
h) $R_1$ denotes chlorine, $R_2$, $R_4$ and $R_5$ denote hydrogen and $R_3$ denotes $CF_3$.

Fluorine-containing acetophenones of the formula (IIIa) with X=hydrogen, which have the meanings of the substituents indicated under c) to h), are preferred. Very particularly preferred fluorine-containing acetophenones of the formula (IIIa) with X=hydrogen are those which have the meanings of the substituents indicated under f) to h), that is to say 2-chloro-3-trifluoromethylacetophenone, 2-chloro-4-trifluoromethylacetophenone and 2-chloro-6-trifluoromethylacetophenone.

Of the acetophenones of the formula (IIIa) halogenated on the $CH_3$, with X=chlorine or bromine, the corresponding compounds are preferred. Very particularly preferred in this connection are 2-chloro-3-trifluoromethylphenacyl bromide and chloride, 2-chloro-4-trifluoromethylphenacyl bromide and chloride and 2-chloro-6-trifluoromethylphenacyl bromide and chloride.

The present invention also relates to a process for the preparation of fluorine-containing acetophenones of the formula (IIIa) which are optionally halogenated on the $CH_3$ group, which is characterized in that, for the preparation of compounds of the formula (IIIa) with X=hydrogen, a fluorinated benzoic acid derivative of the formula (IIIb)

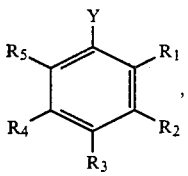

(IIIb)

in which $R_1$ to $R_5$ have the meaning indicated in formula (IIIa) and

Y represents a nitrile group or an acid halide group, is reacted with an organomagnesium compound capable of introducing methyl groups and then a hydrolysis is carried out and, for the preparation of compounds of the formula (IIIa) with X=chlorine or bromine, is subsequently reacted further at −20° to +80° C. with a chlorinating or brominating agent.

Those fluorinated benzoic acid derivatives of the formula (IIIb) in which $R_1$ to $R_5$ have the meanings indicated in formula (IIIa) under c) to h) are preferred for use in the process according to the invention. Particularly preferred fluorinated benzoic acid derivatives are those in which $R_1$ to $R_5$ have the meanings indicated in formula (IIIa) under f) to h).

If Y represents an acid halide group in formula (IIIb), it is preferably an acid fluoride or acid chloride group (COF or COCl), in particular an acid fluoride group (COF).

Y preferably stands for a nitrile group in formula (IIIb).

Fluorinated benzoic acid derivatives of the formula (IIIb) in which Y represents an acid halide group are known (see, for example, German Offenlegungsschrift 3,621,707).

Fluorinated benzoic acid derivatives of the formula (IIIb) in which X represents a nitrile group are in some cases known and in some cases new. New fluorinated benzonitriles are in particular those of the formula (IIIc)

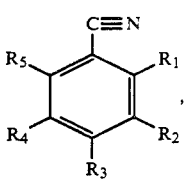

(IIIc)

in which $R_1$, $R_4$ and $R_5$ represent hydrogen and $R_2$ and $R_3$ represent $CF_3$ or $R_1$, $R_4$ and $R_5$ represent hydrogen, $R_2$ represents chlorine and $R_3$ represents $OCF_3$ or $R_2$, $R_3$ and $R_4$ represent hydrogen, $R_1$ represents chlorine and $R_5$ represents $CF_3$.

The present invention therefore also relates to those new fluorinated benzonitriles of the formula (IIIc). Preparation possibilities for the new fluorinated benzonitriles are indicated in Examples 105a), 106a), and 106b) and 109a).

The organomagnesium compounds capable of introducing methyl groups can be, for example, methylmagnesium halides, in particular methylmagnesium bromide or methylmagnesium iodide, or ethoxymagnesiummalonic ester.

The latter is accessible, for example, by reacting magnesium diethoxide with malonic ester and in this way replacing an ethoxy group of the magnesium diethoxide by a malonic ester group. With ethoxymagnesiummalonic ester, a malonic ester radical can be introduced onto the C atom in the radical Y of the fluorinated benzoic acid derivative of the formula (IIIb), which is then converted into a methyl group in the hydrolysis by decarboxylation.

0.8 to 3 moles of the particular organomagnesium compound can be employed, for example, relative to 1 mole of fluorinated benzoic acid derivative of the formula (IIIb). Preferably, this amount is 1 to 1.5 moles. The organomagnesium compound is generally used in dissolved form. Suitable solvents are, for example, ethers, in particular diethyl ether and tetrahydrofuran. In general, a solution of the particular organomagnesium compound is prepared separately and this is added to the compound of the formula (IIIb) which can likewise be present in dissolved form. When using methylmagnesium halides, it may be advantageous to add a small amount of catalyst, for example a copper or iron salt.

The reaction of the benzoic acid derivative of the formula (IIIb) with the organomagnesium compound can be carried out in a wide temperature range, for example between −60° and +100° C. The hydrolysis to be carried out after this reaction can be accomplished, for example, by pouring into or adding water and keeping for several hours at a temperature in the range from −10° to +40° C. An acid is preferably added, for example acetic, hydrochloric or sulphuric acid. Carrying out the hydrolysis in the presence of a strong acid is particularly advantageous if ethoxymagnesiummalonic ester has been employed as an organomagnesium compound.

The reaction mixture present after the hydrolysis can be worked up, for example, by separating the organic phase from this and fractionally distilling the latter.

By means of the reaction of a benzoic acid derivative of the formula (IIIb) with an organomagnesium compound capable of introducing methyl groups together with subsequent hydrolysis, fluorine-containing acetophenones of the formula (IIIa) with X=hydrogen are obtained. Acetophenones of the formula (IIIa) with X=chlorine or bromine halogenated on the $CH_3$ group can be obtained from the latter if they are reacted at −20° to +80° C. with a chlorinating or brominating agent. A suitable chlorinating agent is, for example, sulphuryl chloride ($SO_2Cl_2$); elemental bromine, for example, is suitable as a brominating agent.

In general, the chlorinating or brominating agent is employed in the stoichiometrically required amount or in excess, for example 1 to 1.2 moles per mole of starting material. Suitable reaction temperatures are those in the range −20° to +80° C., in particular those from 0° to 40° C.

The chlorination or bromination can be carried out in the presence or absence of solvents. It is preferably carried out in the presence of inert organic solvents, for example methylene chloride or glacial acetic acid. Likewise, it is not absolutely necessary, but in general advantageous, to work in the presence of catalytic amounts of a strong concentrated mineral acid. Sulphuric acid or hydrochloric acid, for example, are suitable here.

The end of the chlorination or bromination can be detected by gas evolution (hydrogen chloride or bromide) ceasing. The reaction mixture can then be worked up, for example, in such a way that it is mixed with water or ice water and shaken with an organic solvent, the organic extract is concentrated and the residue is distilled. If desired, a further purification can be carried out, for example by recrystallization, distillation or chromatography.

The new fluorine-containing acetophenones of the formula (IIIa) with X=chlorine or bromine can be converted by reaction with a thiourea derivative of the formula (II)

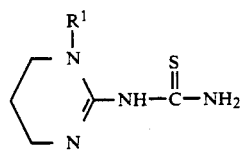

into substituted aminothiazoles of the type

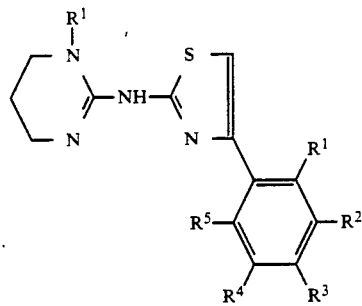

which are compounds which possess a good activity against human and animal pathogenic fungi.

It is to be regarded as surprising that the fluorinated acetophenones of the formula (IIIa) according to the invention are accessible in the described manner in good yields since reactions with the activated halogen atoms bonded to the ring and hydrolysis of the $CF_3$ groups bonded to the ring were to be expected in addition to the desired reaction.

Suitable diluents for carrying out the process according to the invention for the preparation of the 2-aminothiazoles according to the invention are inert organic or inorganic solvents. In particular, these include aliphatic, alicyclic or aromatic, optionally halogenated hydrocarbons, such as, for example, benzine, benzene, toluene, xylene, chlorobenzene, petroleum ether, hexane, cyclohexane, dichloromethane, chloroform, carbon tetrachloride, ethers, such as diethyl ether, dioxane, tetrahydrofuran or ethylene glycol dimethyl ether or ethylene glycol diethyl ether, ketones such as acetone or butanone, nitriles, such as acetonitrile or propionitrile, amides, such as dimethylformamide, dimethylacetamide, N-methylformanilide, N-methylpyrrolidone or hexamethylphosphoric triamide, esters, such as ethyl acetate or sulphoxides, mixtures thereof such as dimethyl sulphoxide, alcohols such as methanol, ethanol or propanol and bases such as pyridine, if desired mixtures thereof with water or pure water.

The process according to the invention is optionally carried out in the presence of a suitable reaction auxiliary. Those which are suitable are all customary inorganic or organic bases. These include, for example, alkali metal hydroxides, such as sodium hydroxide or potassium hydroxide, alkali metal carbonates, such as sodium carbonates, potassium carbonate or sodium hydrogen carbonate, ammonia and primary, secondary or tertiary amines, such as triethylamine, N,N-dimethylaniline, pyridine, N,N-dimethylaminopyridine, diazabicyclooctane (DABCO), diazabicyclononene (DBN) or diazabicycloundecene (DBU).

When carrying out the process according to the invention, the reaction temperatures can be varied within a wide range. In general, the process is carried out at temperatures between 0° C. and 180° C., preferably at temperatures between 20° C. and 150° C.

In order to carry out the process according to the invention, in general 1.0 to 1.5 moles, preferably 1.0 to 1.2 moles of ketone derivative of the formula (III) and, if desired, 1.0 to 1.5 moles, preferably 1.0 to 1.2 moles, of reaction auxiliary are employed per mole of thiourea derivative of the formula (II).

The reaction is carried out and worked up, and the reaction products are isolated by generally customary methods.

The acid addition salts of the compounds of the formula (I) can be obtained in a simple manner by customary salt formation methods, such as, for example, by dissolving a compound of the formula (I) in a suitable inert solvent and adding the acid, such as, for example, hydrochloric acid, and can be isolated in a known manner, for example, by filtering off, and, if desired, can be purified by washing with an inert organic solvent.

The compounds of the formula (I) according to the invention and their acid addition salts exhibit antimicrobial, in particular strong antimycotic, actions. They have a very wide spectrum of antimycotic action, in particular against dermatophytes and Blastomycetes and also biphasic fungi, for example against Candida species, such as *Candida albicans*, Epidermophyton species, such as *Epidermophyton floccosum*, Aspergillus species, such as *Aspergillus niger* and *Aspergillus fumigatus*, Trichophyton species, such as *Trichophyton mentagrophytes*, Microsporon species such as *Microsporon felineum* and Torulopsis species such as *Torulopsis glabrata*. The enumeration of these microorganisms in no case represents a limitation of the combatable microorganisms, but is only of illustrative character.

Examples of indications in human medicine which may be mentioned, for example, are:

Dermatomycoses and systemicmycoses caused by *Trichophyton mentagrophytes* and other Trichophytone species, Microsporon species and epidermophyton floccosum, Blastomycetes and biphasic fungi and also Hyphomycetes.

Areas of indication in veterinary medicine which may be mentioned, for example, are:

All dermatomycoses and systemicmycoses, in particular those which are caused by the abovementioned pathogens.

The present invention includes pharmaceutical preparations which contain one or more active compounds according to the invention or which consist of one or more active compounds according to the invention in addition to non-toxic, inert pharmaceutically suitable excipients.

The present invention also includes pharmaceutical preparations in dosage units. This means that the preparations are present in the form of individual parts, for example tablets, coated tablets, capsules, pills, suppositories and ampoules, the active compound content of which corresponds to a fragment or a multiple of an individual dose. The dosage units may contain, for example, 1, 2, 3 or 4 individual doses or $\frac{1}{2}$, $\frac{1}{3}$ or $\frac{1}{4}$ of an individual dose. An individual dose preferably contains the amount of active compound which is administered in one administration and which usually corresponds to a whole, a half, a third or a quarter of a daily dose.

Non-toxic, inert pharmaceutically suitable excipients are taken to mean solid, semisolid or liquid diluents, fillers or formulation auxiliaries of any type.

Preferred pharmaceutical preparations which may be mentioned are tablets, coated tablets, capsules, pills, granules, suppositories, solutions, suspensions and emulsions, pastes, ointments, gels, creams, lotions, powders or sprays.

Tablets, coated tablets, capsules, pills and granules may contain the customary excipients, such as (a) fillers and extenders, for example starches, lactose, sucrose, glucose, mannitol and silica, (b) binders, for example carboxymethylcellulose, alginates, gelatin, polyvinylpyrrolidone, (c) humectants, for example glycerol, (d) disintegrants, for example agar-agar, calciumcarbonate and sodium bicarbonate, (e) solution retardants, for example paraffin and (f) absorption accelerators, for example quarternary ammonium compounds, (g) wetting agents, for example cetyl alcohol, glycerol monostearate, (h) adsorption agents, for example kaolin and bentonite and (i) lubricants, for example talc, calcium stearate and magnesium stearate and solid polyethylene glycols or mixtures of the substances mentioned under (a) to (i) in addition to the active compound or compounds.

The tablets, coated tablets, capsules, pills and granules may be provided with the customary coatings and coverings, optionally containing opacifying agents, and may be composed so that they deliver the active compound or compounds only or preferably into a certain part of the intestinal tract, if desired in a sustained manner, it being possible to use, for example, polymeric substances and waxes as embedding materials.

The active compound or compounds may optionally also be present in microencapsulated form with one or more of the abovementioned excipients.

Suppositories may contain the customary water-soluble or water-insoluble excipients, for example polyethylene glycols, fats, for example cocoa fat and higher esters (for example $C_{14}$ alcohol with $C_{16}$ fatty acid) or mixtures of these substances in addition to the active compound or compounds.

Ointments, pastes, creams and gels may contain the customary excipients, for example animal and vegetable fats, waxes, paraffins, starch, tragacanth, cellulose derivatives, polyethylene glycols, silicones, bentonites, silica, talc and zinc oxide or mixtures of these substances in addition to the active compound or compounds.

Powders and sprays may contain the customary excipients, for example lactose, talc, silica, hydrated alumina, calcium silicate and polyamide powder or mixtures of these substances and sprays may additionally contain the customary propellants, for example chlorofluorohydrocarbons, in addition to the active compound or compounds.

Solutions and emulsions may contain the customary excipients such as solvents, solution retardants and emulsifiers, for example water, ethyl alcohol, isopropyl alcohol, ethyl carbonate, ethyl acetate, benzyl alcohol, benzyl benzoate, propylene glycol, 1,3-butylene glycol, dimethylformamide, oils, in particular cotton seed oil, groundnut oil, maize germ oil, olive oil, castor oil and sesame oil, glycerol, glycerol formal, tetrahydrofurfuryl alcohol, polyethylene glycols and fatty acid esters of sorbitan or mixtures of these substances in addition to the active compound or compounds.

For parenteral administration, the solutions and emulsions may also be present in sterile and blood-isotonic form.

Suspensions may contain the customary excipients, such as liquid diluents, for example water, ethyl alcohol, propyl alcohol, suspending agents, for example ethoxylated isostearyl alcohols, polyoxyethylene sorbitol and sorbitan esters, microcrystalline cellulose, aluminium metahydroxide, bentonite, agar-agar and tragacanth or mixtures of these substances in addition to the active compound or compounds.

The formulation forms mentioned may also contain colorants, preservatives and also odor-enhancing and flavor-enhancing additives, for example peppermint oil and eucalyptus oil, and sweeteners, for example saccharin.

The therapeutically active compounds should preferably be present in the abovementioned pharmaceutical preparations in a concentration from about 0.1 to 99.5, preferably from 0.5 to 95% by weight of the total mixture.

The abovementioned pharmaceutical preparations may also contain other pharmaceutical active compounds in addition to the active compounds according to the invention.

The abovementioned pharmaceutical preparations are prepared in a customary manner by known methods, for example by mixing the active compound or compounds with the excipient or excipients.

The present invention also includes the use of the active compounds according to the invention and also pharmaceutical preparations which contain one or more active compounds according to the invention in human and veterinary medicine for the prevention, amelioration and/or cure of the abovementioned diseases.

The active compounds or the pharmaceutical preparations may be administered locally, orally, parenterally, intraperitoneally and/or rectally, preferably parenterally, in particular intravenously.

In general, it has proved advantageous both in human and in veterinary medicine to administer the active compound or compounds according to the invention in total amounts from about 2.5 to about 200, preferably from 5 to 150 mg/kg of body weight every 24 hours, if desired in the form of a number of individual doses to attain the desired results.

On oral administration, the active compounds according to the invention are administered in total amounts from about 2.5 to about 200, preferably from 5 to 150 mg/kg of body weight every 24 hours and on parenteral administration in total amounts of about 2.5 to about 50, preferably of 1 to 25 mg/kg of body weight every 24 hours.

However, it may be necessary to deviate from the dosages mentioned, depending on the species and the body weight of the subject to be treated, the nature and severity of the disease, the type of the preparation and the administration of the medicament and the time period or interval within which administration takes place. Thus, in some cases it may be sufficient to manage with less than the abovementioned amount of active compound, whereas in other cases the abovementioned amount of active compound must be exceeded. The optimum dosage required in each case and the type of administration of the active compound can easily be established by any person skilled in the art on the basis of his expert knowledge.

PREPARATION EXAMPLES

Example 1

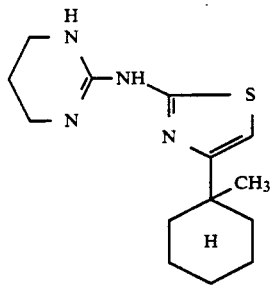

15.8 g (0.1 mol) of N-(1,4,5,6-tetrahydro-2-pyrimidinyl)-thiourea are added to 17.45 g (1 mol) of chloromethyl 1-methylcyclohexyl ketone (compare, for example EP-A-55,427; German Offenlegungsschrift 3,145,857) in 100 ml of acetone and the mixture is heated to reflux temperature for 2 hours. After cooling to room temperature, the precipitated product is filtered off with suction and purified by chromatography on silica gel (eluant: toluene/ethanol 1:1).

After recrystallization from ethanol, 18.1 g (65% of theory) of 4-(1-methylcyclohexyl)-2-[N-(1,4,5,6-tetrahydro-2-pyrimidinyl)amino]thiazole of melting point 139° C.-140° C. are obtained.

Example 2

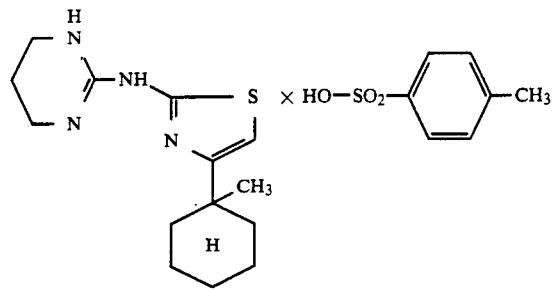

8.94 ml (0.052 mol) of p-toluenesulphonic acid are added to 13.9 g (0.05 mol) of 4-(1-methylcyclohexyl)-2-[N-(1,4,5,6-tetrahydro-2-pyrimidinyl)amino]thiazole in a mixture of 150 ml of ethanol and 50 ml of toluene, the mixture is heated to 70° C. for 1 hour and concentrated in a water pump vacuum, the residue is stirred with ethylacetate and filtered off with suction, and the solid thus obtained is dried.

27.7 g (89% of theory) of 4-(1-methylcyclohexyl)-2-[N-1,4,5,6-tetrahydro-2-pyrimidinyl)amino]thiazole p-toluenesulphonate.salt of melting point 129° C.-130° C. are obtained.

Example 3

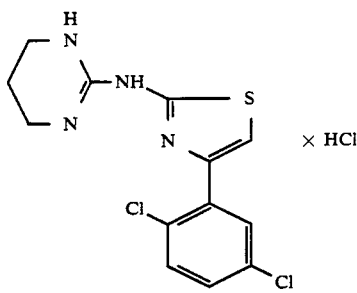

5.8 g (0.1 mol) of N-(1,4,5,6-tetrahydro-2-pyrimidinyl)thiourea are added to 22.35 g (0.1 mol) of 2,5-dichlorophenacyl chloride (compare, for example, Pharmazie 31, 351-354 [1976]; NL 68/7990) in 100 ml of acetone, the mixture is heated to reflux temperature for 2 hours and cooled to room temperature, and precipitated product is filtered off with suction, washed with acetone and dried.

34 g (94% of theory) of 4-(2,5-dichlorophenyl)-2-[N-(1,4,5,6-tetrahydro-2-pyrimidinyl)amino]thiazole hydrochloride of melting point 247° C.-248° C. are obtained.

Example 4

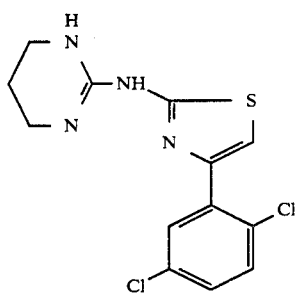

18.18 g (0.05 mol) of 4-(2,5-dichlorophenyl)-2-[N-(1,4,5,6-tetrahydro-2-pyrimidinyl)amino]thiazole hydrochloride are stirred at room temperature for 30 minutes with 300 ml of 1N sodium hydroxide solution; the solid thus obtained is filtered off with suction, washed until neutral with water and dried.

34 g (91% of theory) of 4-(2,5-dichlorophenyl)-2-[N-(1,4,5,6-tetrahydro-2-pyrimidinyl)amino]thiazole of melting point 188° C.–189° C. are obtained.

The following substituted 2-aminothiozoles of the general formula (I) are obtained in a corresponding manner and according to the general instructions for preparation:

TABLE 1

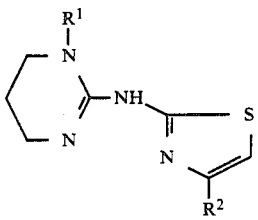
(I)

| Ex. No. | $R^1$ | $R^2$ | Acid addition salt with | Melting point (°C.) |
|---|---|---|---|---|
| 5 | H | 1-methylcyclohexyl | 2-(benzoylamino)benzenesulfonamide derivative | 159–160 |
| 6 | H | 1-methylcyclohexyl | $CH_3$—$SO_3H$ | 140–141 |
| 7 | H | 2,3-dimethylphenyl | HCl | 241–242 |
| 8 | H | 3-methylphenyl | HCl | 289–290 |
| 9 | H | 2,4-dichlorophenyl | 2-(benzoylamino)benzenesulfonamide derivative | 289–290 |
| 10 | H | 2,4-dichlorophenyl | $H_3C$—$C_6H_4$—$SO_3H$ | 125–126 |

TABLE 1-continued
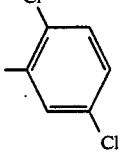
(I)
| Ex. No. | R¹ | R² | Acid addition salt with | Melting point (°C.) |
|---|---|---|---|---|
| 11 | H | 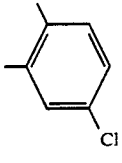 | CH₃SO₃H | 213–214 |
| 12 | H | 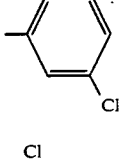 | HBr | 247–248 |
| 13 | H | 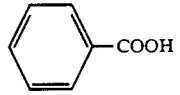 | 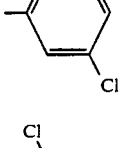 | 138–140 |
| 14 | H | 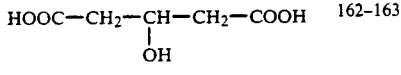 | HOOC—CH₂—CH—CH₂—COOH<br>　　　　　　OH | 162–163 |
| 15 | H | 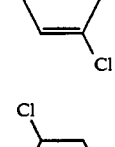 | 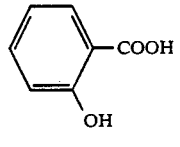 | 157–158 |
| 16 | H | 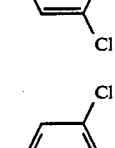 | 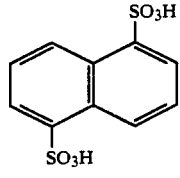 | 296–297 |
| 17 | H | 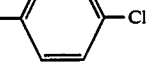 | — | 252–253 |
| 18 | H | 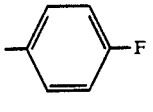 | HCl | 276–277 |

TABLE 1-continued
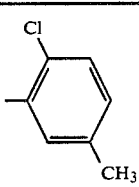
(I)
| Ex. No. | R¹ | R² | Acid addition salt with | Melting point (°C.) |
|---|---|---|---|---|
| 19 | H | 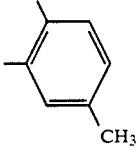 4-Cl, 3-CH₃ phenyl | HCl | 190–191 |
| 20 | H | 4-Cl, 3-CH₃ phenyl | — | 194–195 |
| 21 | H | 4-Cl, 3-CH₃ phenyl | HBr | 239–240 |
| 22 | H | 4-Cl, 3-CH₃ phenyl | 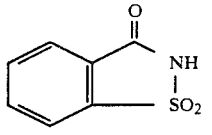 saccharin | 230–231 |
| 23 | H | 4-Cl, 3-CH₃ phenyl | 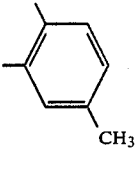 H₃C—C₆H₄—SO₃H | 212–213 |
| 24 | H | 4-Cl, 3-CH₃ phenyl | CH₃—SO₃H | 203–204 |
| 25 | H | 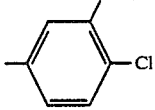 2-CH₃, 4-Cl phenyl (or similar) | HCl | 216–217 |

TABLE 1-continued

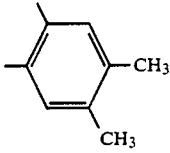
(I)

| Ex. No. | R¹ | R² | Acid addition salt with | Melting point (°C.) |
|---|---|---|---|---|
| 26 | H | Cl, CH₃, CH₃ (substituted phenyl)  | HCl | 207–208 |
| 27 | H | Cl (substituted phenyl)  | HCl | oil |
| 28 | H | Cl (substituted phenyl)  | HBr | 212–213 |
| 29 | H | Cl (substituted phenyl)  | — | 174 |
| 30 | H | Cl (substituted phenyl) 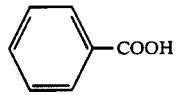 | $CH_3-SO_3H$ | 195 |
| 31 | H | Cl (substituted phenyl)  | 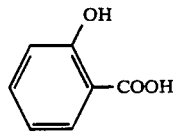 COOH | 154 |
| 32 | H | Cl (substituted phenyl)  |  OH, COOH | 171–172 |
| 33 | H | Cl (substituted phenyl) | $HOOC-CH_2-CH-CH_2-COOH$ <br> $\quad\quad\quad\quad\quad\quad\ \ OH$ | 150 |
| 34 | H | Cl, Cl, Cl (substituted phenyl) 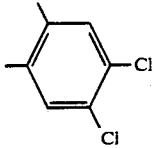 | HCl | 311–312 |

TABLE 1-continued (I)

| Ex. No. | R¹ | R² | Acid addition salt with | Melting point (°C.) |
|---|---|---|---|---|
| 35 | H | 3-methylphenyl | HBr | 234 |
| 36 | H | 4-ethylphenyl | HBr | 205–206 |
| 37 | H | 3,4-dichloro-methylphenyl | HBr | 288–289 |
| 38 | H | 3,4-dichloro-methylphenyl | — | 222–223 |
| 39 | H | 3,4-dichloro-methylphenyl | HCl | 267–268 |
| 40 | H | 3,4-dichloro-methylphenyl | saccharin (2-sulfobenzamide) | 238–239 |
| 41 | H | 3,4-dichloro-methylphenyl | CH₃-C₆H₄-SO₃H | 196–197 |
| 42 | H | 3,4-dichloro-methylphenyl | CH₃—SO₃H | 222–223 |

TABLE 1-continued (I) Structure: R¹-N(ring)-NH-C(=N-)-thiazole with R² on thiazole

| Ex. No. | R¹ | R² | Acid addition salt with | Melting point (°C.) |
|---|---|---|---|---|
| 43 | H | 2,4-dimethylphenyl | HBr | 208–209 |
| 44 | H | 2,3,4,6-tetramethylphenyl | HBr | 244–245 |
| 45 | H | 2,4,6-trimethylphenyl | HBr | 216–217 |
| 46 | H | 2,3-dichlorophenyl | HBr | 227–228 |
| 47 | H | 2,3-dichlorophenyl | — | 213 |
| 48 | H | 2,3-dichlorophenyl | HCl | 236–237 |
| 49 | H | 2,3-dichlorophenyl | saccharin (2-sulfobenzoic imide) | 241 |
| 50 | H | 2,3-dichlorophenyl | p-toluenesulfonic acid (CH₃-C₆H₄-SO₃H) | 157 |

TABLE 1-continued (I) [Structure: R¹-N in ring with NH-C(=N)-thiazole bearing R²]

| Ex. No. | R¹ | R² | Acid addition salt with | Melting point (°C.) |
|---|---|---|---|---|
| 51 | H | 2,3-dichlorophenyl | CH₃—SO₃H | 215–216 |
| 52 | H | 2,3-dichlorophenyl | 2-hydroxybenzoic acid (salicylic acid) | 141 |
| 53 | H | 2,3-dichlorophenyl | HOOC—CH₂—CH₂—COOH | 137 |
| 54 | H | 3-chlorophenyl | HCl | 223–224 |
| 55 | H | 2,3-dimethylphenyl | HCl | 270–271 |
| 56 | H | 3,5-dichlorophenyl | HCl | 267 |
| 57 | H | 3,4-dichlorophenyl (with additional Cl) | HCl | 287–288 |
| 58 | H | 3-chloro-2-methyl-5-fluorophenyl | HCl | 282–283 |

TABLE 1-continued (I)

[Structure: Guanidine-thiazole compound with R¹ on N, N-NH linkage to thiazole bearing R² substituent]

| Ex. No. | R¹ | R² | Acid addition salt with | Melting point (°C.) |
|---|---|---|---|---|
| 59 | H | 2,6-difluoro-3-methylphenyl (F, CH₃, F) | HCl | 251–252 |
| 60 | H | 2,4-dichloro-5-methylphenyl (CH₃, Cl, Cl) | HCl | 282–283 |
| 61 | H | 2,3,4-trichlorophenyl (Cl, Cl, Cl) | HCl | 295–296 |
| 62 | H | 4-OCF₃-phenyl | HBr | 236 |
| 63 | H | 4-SCF₃-phenyl | HBr | 260 |
| 64 | H | 3-CF₃-phenyl | HBr | 250–251 |
| 65 | H | 3-CF₃-phenyl | — | 230 |
| 66 | H | 3-CF₃-phenyl | HCl | 239–240 |
| 67 | H | 3-CF₃-phenyl | 2-(aminosulfonyl)benzamide (saccharin) | 233–234 |

TABLE 1-continued (I) [Structure: R¹-N in ring with guanidine linked to thiazole bearing R²]

| Ex. No. | R¹ | R² | Acid addition salt with | Melting point (°C.) |
|---|---|---|---|---|
| 68 | H | 3-CF₃-phenyl | CH₃-C₆H₄-SO₃H | 187–188 |
| 69 | H | 3-CF₃-phenyl | CH₃—SO₃H | 166 |
| 70 | H | 3-CF₃-phenyl | 2-OH-C₆H₄-COOH | 179 |
| 71 | H | cyclohexyl | HBr | 190 |
| 72 | H | 2-CF₃-4-Cl-phenyl | HBr | 264–265 |
| 73 | H | 2-Cl-4-CF₃-phenyl | HBr | 256–257 |
| 74 | H | 4-C(CH₃)₃-phenyl | HCl | 143–145 |
| 75 | H | 2,4-F₂-phenyl | HCl | 234–235 |
| 76 | H | 2-CF₃-phenyl | HBr | 227–228 |

TABLE 1-continued
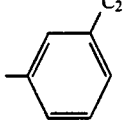
(I)
| Ex. No. | R¹ | R² | Acid addition salt with | Melting point (°C.) |
|---|---|---|---|---|
| 77 | H | 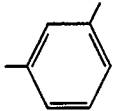 C₂H₅ | HBr | 213–214 |
| 78 | H | 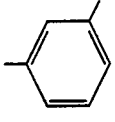 C₂H₅ | — | 198–199 |
| 79 | H | 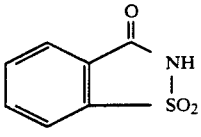 C₂H₅ | HCl | 198 |
| 80 | H | 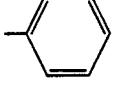 C₂H₅ | 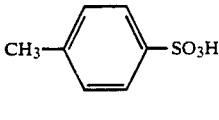 | 199 |
| 81 | H | 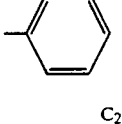 C₂H₅ | CH₃—⌬—SO₃H | 141–142 |
| 82 | H | 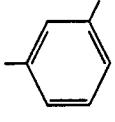 C₂H₅ | CH₃—SO₃H | 157 |
| 83 | H | 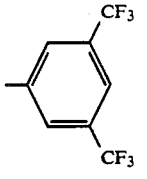 CF₃, CF₃ | HBr | 289–290 |
| 84 | H | 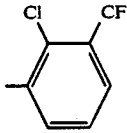 Cl, CF₃ | HBr | 188–189 |
| 85 | H | 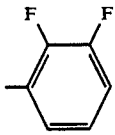 F, F | HBr | 261 |

TABLE 1-continued

Structure (I): A 1,4,5,6-tetrahydropyrimidine with R¹ on N1, connected via NH to a thiazole bearing R² at the 4-position.

| Ex. No. | R¹ | R² | Acid addition salt with | Melting point (°C.) |
|---|---|---|---|---|
| 86 | H | 3-Cl-4-CF₃-phenyl | HBr | 288–289 |
| 87 | H | 3-Cl-4-CF₃-phenyl (isomer) | HBr | 270–271 |
| 88 | H | 2-CF₃-phenyl | — | 192 |
| 89 | H | 2-CF₃-phenyl | CH₃—SO₃H | 196 |
| 90 | H | 2,6-difluorophenyl | HBr | 251 |
| 91 | H | pentafluorophenyl | HBr | >250 |
| 92 | H | 3,4-difluorophenyl | — | 229–231 |
| 93 | H | 3,4-difluorophenyl | CH₃—SO₃H | 229 |
| 94 | H | 2,2,3,3-tetrafluoro-benzo[1,4]dioxine | — | 238–239 |

TABLE 1-continued (I)

| Ex. No. | R¹ | R² | Acid addition salt with | Melting point (°C.) |
|---|---|---|---|---|
| 95 | H | 3,4-(OCF₂CF₂O)-phenyl | CH₃—SO₃H | 236 |
| 96 | H | 2,4-difluorophenyl | — | 198–199 |
| 97 | H | 3,4-(OCF₂O)-phenyl | HCl | 231 |
| 98 | H | 3,4-(OCF₂O)-phenyl | — | >250 |
| 99 | H | 3,4-(OCF₂O)-phenyl | CH₃—SO₃H | 200 (dec.) |
| 100 | H | pentafluorophenyl | H₃PO₄ | 221 |
| 101 | H | 2-Cl-3-CF₃-phenyl | — | 199 |
| 102 | H | 2,3,5-trifluoro-6-CF₃-phenyl | — | >250 |
| 103 | H | 2,4,5-trifluorophenyl | — | 244 |

TABLE 1-continued

[Structure (I): cyclic amidine with R¹ on N, connected via NH to thiazole bearing S and R² substituent]

| Ex. No. | R¹ | R² | Acid addition salt with | Melting point (°C.) |
|---|---|---|---|---|
| 104 | H | 2,4,5-trifluorophenyl | HCl | >250 |
| 105 | H | 2,3,4,5,6-pentafluorophenyl | — | 247 |

Intermediates

Example 106 a) 3,4-Bistrifluoromethylbenzonitrile 229 g (1 mol) of 3,4-bistrifluoromethylaniline were diazotized in a solution of 350 g of concentrated sulphuric acid in 1.25 l of water using 70 g of sodium nitrite in 140 ml of water. After the diazonium salt solution became nitrite-free, it was added dropwise to a solution warmed to 100° C. consisting of 550 ml of water, 210 g of sodium cyanide, 10 g of copper(I) cyanide, 500 g of sodium hydrogencarbonate and 9 g of nickel sulphate x 7 $H_2O$. The product was isolated from the reaction mixture by steam distillation and subsequently distilled again. 152 g of product having a boiling point at 14 mbar of 85° C. and a melting point of 71° to 72° C. were obtained. This corresponds to a yield of 63% of theory.

b) 3,4-Bistrifluoromethylacetophenone 119.5 g (0.5 mol) of 3,4-bistrifluoromethylbenzonitrile were heated to reflux for 3 hours with 166 g (1 mol) of methyl magnesium iodide in 750 ml of benzene. After cooling to 0°, 500 ml of 6 N aqueous hydrochloric acid were allowed to flow in and the mixture was heated to reflux for a further 6 hours. The mixture was then cooled, and the organic phase was separated off and distilled. 123 g of product having a boiling point at 0.3 mbar of 71° to 73° C. were obtained. This corresponds to a yield of 48% of theory.

Example 107 a) 3-Chloro-4-trifluoromethoxybenzamide 242.5 g (1 mol) of 3-chloro-4-trifluoromethoxybenzoyl fluoride were allowed to drop into 500 ml of 25% strength by weight aqueous ammonia solution with ice cooling, then the mixture was stirred for 30 minutes and the precipitate which deposited was filtered off with suction. 227 g of product having a melting point of 98° C. were obtained. This corresponds to a crude yield of 95% of theory.

b) 3-Chloro-4-trifluoromethoxybenzonitrile 750 ml of $SOCl_2$ were added to 239.5 g (1 mol) of 3-chloro-4-trifluoromethoxybenzamide and the mixture was heated slowly (corresponding to the evolution of gas) to 85° C. The mixture was then fractionally distilled and 189 g of product having a boiling point at 13 mbar of 96° C. and a melting point of 38° to 40° C. were obtained. This corresponds to a yield of 85% of theory.

c) 3-Chloro-4-trifluoromethoxyacetophenone

Analogously to Example 1b), 221.5 g (1 mol) of 3-chloro-4-trifluoromethoxybenzonitrile were reacted with methylmagnesium iodide and the reaction mixture was worked up correspondingly. 105.4 g of product having a boiling point at 0.1 mbar of 98° to 99° C. were obtained. This corresponds to a yield of 44% of theory.

Example 108

3-Chloro-4-trifluoromethylacetophenone 226 g (1 mol) of 3-chloro-4-trifluoromethylbenzoyl fluoride were initially introduced into 500 ml of diethylether and, after adding 3 g of $FeCl_3$, a Grignard solution prepared from 95 g (1 mol) of methyl bromide and 24.3 g of magnesium in 250 ml diethyl ether was added dropwise at an internal temperature of −60° C. in the course of 4 hours. The mixture was kept for a further 24 hours at −60° C. then warmed to 25° C. The reaction mixture was then poured into water, and the organic phase was separated off and fractionally distilled. 47.5 g of product having a boiling point at 0.2 mbar of 84° to 87° C. were obtained. This corresponds to a yield of 20% of theory.

Example 109

2-Chloro-4-trifluoromethylacetophenone 81 g (0.358 mol) of 2-chloro-4-trifluoromethylbenzoyl chloride were reacted with methylmagnesium bromide analogously to Example 3 and the reaction mixture was worked up correspondingly. 35.2 g of product having a boiling point at 10 mbar of 80° to 81° C. were obtained. This corresponds to a yield of 44% of theory.

Example 110 a) 2-Chloro-6-trifluoromethylbenzonitrile 255 g (1 mol) of 2-chloro-6-trichloromethylbenzonitrile and 250 g of anhydrous hydrogen fluoride were heated to 140° C. for 4 hours in an autoclave. The resulting hydrogen chloride was allowed to escape continuously at 25 bar. Excess hydrogen fluoride was then stripped off, the reaction residue was distilled, the distillate was collected in a boiling range from 80° to 142° C. at 15 mbar (180 g), 55 g of antimony trifluoride was added to this and the mixture was heated to 90° C. A small amount of chlorine was passed into the hot reaction mixture at 90° C. in order to activate the antimony trifluoride. The mixture was then heated to 135° C. for 1 hour more. To work up, the reaction mixture was poured into water, and the organic phase was separated off and distilled. 138 g of product having a boiling point at 13 mbar of 112° to 113° C. and a melting point of 45° to 47° C. were obtained. This corresponds to a yield of 67% of theory.

b) 2-Chloro-6-trifluoromethylacetophenone 154 g (0.75 mol) of 2-chloro-6-trifluoromethylbenzonitrile were initially introduced into 375 ml of diethyl ether and, after adding 1 g of CuCl, a Grignard solution prepared from 24.3 g of magnesium and 95 g (1 mol) of methyl bromide in 250 ml of diethyl ether was added dropwise at 28° to 30° C. in the course of 3 hours. The reaction mixture was then stirred at 28° to 30° C. for a further 5 hours. It was then poured into water, and the organic phase was separated off and distilled. 114 g of product having a boiling point at 0.3 mbar of 65° to 66° C. were obtained. This corresponds to a yield of 68% of theory.

Example 111

2-Chloro-3-trifluoromethylacetophenone 193 g (0.94 mol) of 2-chloro-3-trifluoromethylbenzonitrile were reacted with methylmagnesium bromide analogously to Example 5 and the reaction mixture was worked up correspondingly. 94 g of product having a boiling point at 8 mbar of 90° to 91° C. were obtained. This corresponds to a yield of 45% of theory.

Example 112

2,4,5-Trifluoroacetophenone 194.5 g (1 mol) of 2,4,5-trifluorobenzoyl chloride were initially introduced into 100 ml of diethyl ether and heated to boiling under reflux. 1.1 mol of ethoxymagnesium malonic ester dissolved in 100 ml of ethanol and 125 ml of diethyl ether were then allowed to drop in in the course of 30 minutes and the mixture was stirred for 1 hour under reflux. After cooling, the reaction mixture was stirred into 500 ml of ice water and adjusted to a pH of 1 with concentrated sulphuric acid, and the organic material (345 g) was separated off. This organic material was dissolved in 300 ml of acetic acid and, after adding 37.5 ml of concentrated sulphuric acid, heated to reflux until evolution of $CO_2$ had ended, which took 6 hours. The reaction mixture was then cooled and poured into water, and the organic phase was separated off and distilled. 83 g of product having a boiling point at 10 mbar of 63° to 64° C. were obtained. This corresponds to a yield of 47% of theory.

Example 113

2,3,5,6-Tetrafluoro-4-trifluoromethylacetophenone 364 g (1 mol) of 2,3,5,6-tetrafluoro-4-trifluoromethylbenzoyl fluoride were reacted with ethoxymagnesium malonic ester analogously to Example 7 and the reaction mixture was worked up correspondingly. 170 g of product having a boiling point at 60 mbar of 98° to 100° C. were obtained. This corresponds to a yield of 65% of theory.

Examples 114–120

General working procedure 22.4 g (0.14 mol) of bromine dissolved in 50 ml of glacial acetic acid were added dropwise at room temperature (22° C.) in the course of 2 hours in 250 ml of glacial acetic acid to which 1.25 ml of concentrated hydrochloric acid had been added, to 0.125 mol of a compound of the formula (IIIa) with X=hydrogen. The reaction mixture was stirred for a further 2 hours at room temperature. It was then poured into 1 l of ice water, the organic phase was separated off, the aqueous phase was extracted twice using 100 ml each of dichloromethane, and the combined organic phases were washed twice with 150 ml each of water and dried over magnesium sulphate. The solvent was then stripped off in a water pump vacuum. The particulars of the reactions carried out are evident from Table 1, as is the characterization carried out by taking the $^1$H-NMR spectrum (in $CDCl_3$ using tetramethylsilane as the internal standard) of the product obtained (the δ value in ppm for the protons of the —$CH_2$—X group is indicated in each case).

TABLE 2

| Example No. | Product employed obtained according to Example | Reaction product of the formula (IIIa) with X = bromine substituents not mentioned are hydrogen) | Yield [% of theory] | Characterization |
| --- | --- | --- | --- | --- |
| 114 | 105b | $R_2 = R_3 = CF_3$ | 83,8 | 5,30 |
| 115 | 106c | $R_2 = Cl, R_3 = OCF_3$ | 76,9 | 5,33 |

TABLE 2-continued

| Example No. | Product employed obtained according to Example | Reaction product of the formula (IIIa) with X = bromine substituents not mentioned are hydrogen) | Yield [% of theory] | Characterization |
|---|---|---|---|---|
| 116 | 107 | $R_2 = Cl, R_3 = CF_3$ | 81,2 | 5,31 |
| 117 | 108 | $R_1 = Cl, R_3 = CF_3$ | 78,8 | 5,31 |
| 118 | 109b | $R_1 = Cl, R_5 = CF_3$ | 71 | 5,34 |
| 119 | 110 | $R_1 = Cl, R_2 = CF_3$ | 89 | 5,36 |
| 120 | 111 | $R_1 = R_2 = R_4 = R_5 = F$; $R_3 = CF_3$ | 94,3 | 5,20 |

Example 121

40.8 g (0 3 mol) of sulphuryl chloride were added dropwise at room temperature (22° C.) to 48 g (0.275 mol) of 2,4,5-trifluoroacetophenone (obtained according to Example 110) dissolved in 400 ml of dichloromethane and the mixture was stirred until evolution of hydrogen chloride had ended (about 2 hours). The reaction mixture was then added to 600 ml of water, the organic phase was separated off, this was washed until neutral with sodium hydrogen carbonate solution and dried over magnesium sulphate, and the solvent was stripped off in a water pump vacuum. 48.6 g of 2,4,5-trifluorophenacyl chloride were obtained as an oily residue, which corresponds to 84.5% of theory. The characterization of the product carried out as in Examples 113 to 119 yielded a & value of 5.29 ppm.

Use examples

The compounds shown below were employed as comparison substances in the following use examples:

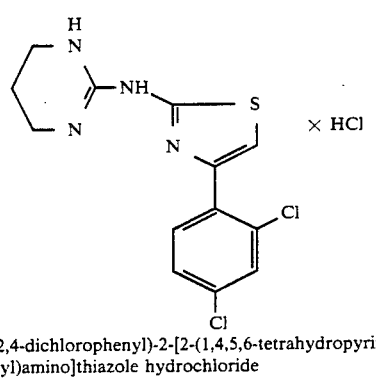

4-(2,4-dichlorophenyl)-2-[2-(1,4,5,6-tetrahydropyrimidinyl)amino]thiazole hydrochloride

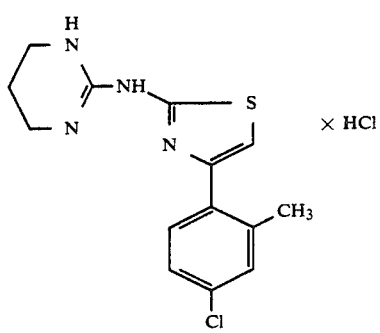

4-(4-chloro-2-methylphenyl)-2-[2-(1,4,5,6-tetrahydropyrimidinyl)amino]thiazole hydrochloride

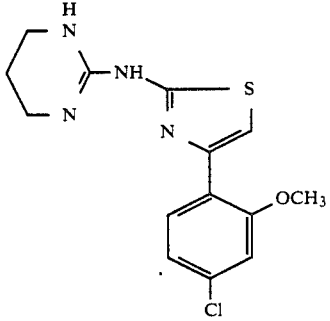

4-(4-chloro-2-methoxyphenyl)-2-[2-(1,4,5,6-tetrahydropyrimidinyl)amino]thiazole (all known from German Offenlegungsschrift 3,220,118)

Example A

Antimycotic in vitro activity

Experimental description:

The in vitro tests were carried out using inocula of microorganisms of on average $5 \times 10^3$ microorganisms/ml of substrate. Kimmig medium was used as nutrient medium for yeasts and yeast nitrogen base medium for Hyphomycetes and Dermatophytes.

The incubation temperature was 37° C. with yeasts and 28° C. with Hyphomycetes and Dermatophytes, and the incubation period was 72 hours with yeasts and 96 to 120 hours with dermatophytes and Hyphomycetes.

The evaluation of the fungicidal action was carried out by plating out and renewed incubation of completely inhibited batches which contain fungicidal concentrations of less than 100 microorganisms c.f.u. (colony forming unit) per ml.

In this test, the compounds of the formula (I) according to the invention according to preparation examples (18), (25), (37), (45), (59), (64) and (75) show a considerably better antimycotic activity than the comparison compounds (A), (B) and (C) known from the prior art.

TABLE A
Antimycotic in vitro activity
MIC[*)] values in μg/ml of nutrient medium
| Active compound | Trichophyton mentagr. | Candida albicans | Aspergillus fumigatus |
|---|---|---|---|
| (A) (known) 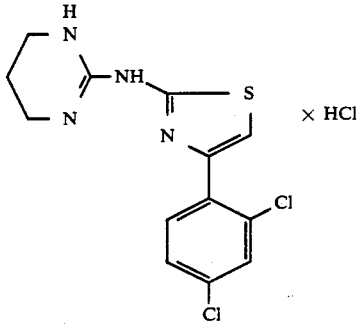 | 16 | 16 | 64 |
| (B) (known) 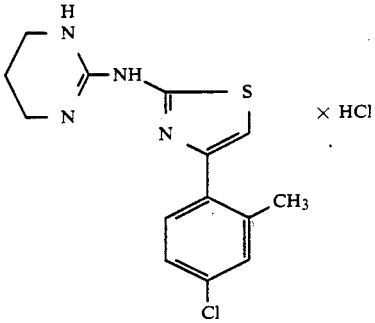 | 16 | 64 | 64 |
| (C) (known) 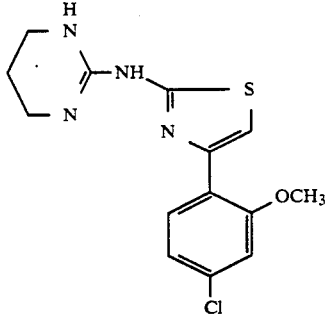 | >64 | >64 | >64 |
| (18) 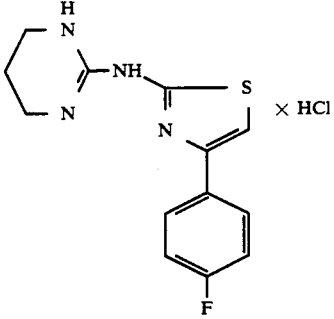 | 8 | >64 | 16 |

TABLE A-continued

Antimycotic in vitro activity

MIC*) values in μg/ml of nutrient medium

| Active compound | Trichophyton mentagr. | Candida albicans | Aspergillus fumigatus |
|---|---|---|---|
| (25) [structure: tetrahydropyrimidinyl-amino thiazole with 4-chloro-3-methylphenyl × HCl] | 4 | 32 | 8 |
| (37) [structure: tetrahydropyrimidinyl-amino thiazole with 4,5-dichloro-2-methylphenyl × HBr] | 2 | 16 | 2 |
| (45) [structure: tetrahydropyrimidinyl-amino thiazole with 2,4,5-trimethylphenyl × HBr] | 8 | 64 | 16 |
| (59) [structure: tetrahydropyrimidinyl-amino thiazole with 2,4-difluoro-3-methylphenyl × HCl] | 4 | 64 | 16 |

TABLE A-continued
Antimycotic in vitro activity
MIC*) values in μg/ml of nutrient medium
| Active compound | Trichophyton mentagr. | Candida albicans | Aspergillus fumigatus |
|---|---|---|---|
| (64) 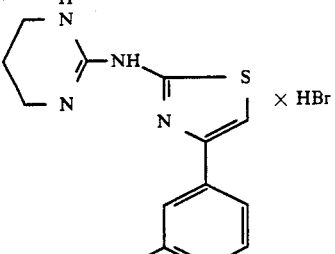 × HBr | 1 | >64 | 4 |
| (75) 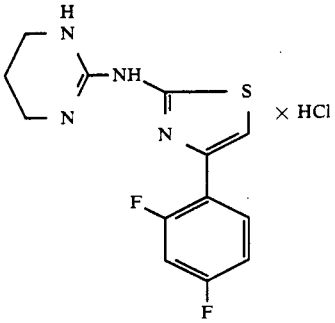 × HCl | 4 | >64 | 32 |
*)minimum fungicidal concentration having a destruction rate of >99%
What is claimed is:
1. A 2-aminothiazole having the following formula
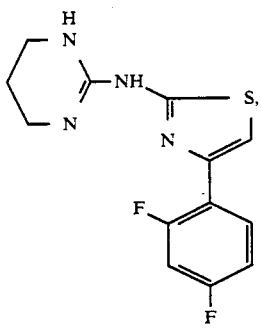
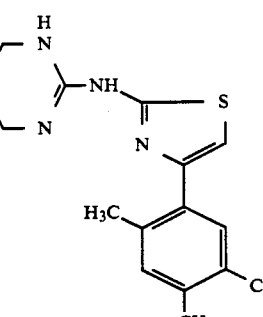
-continued
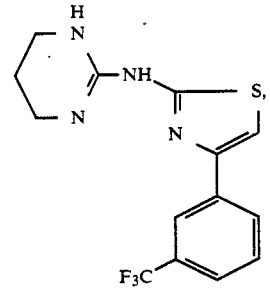
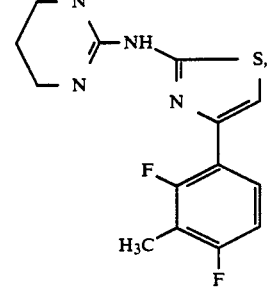
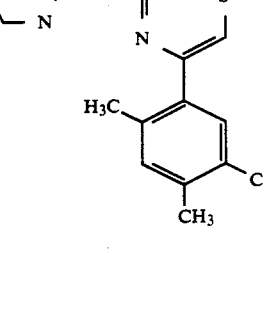

-continued

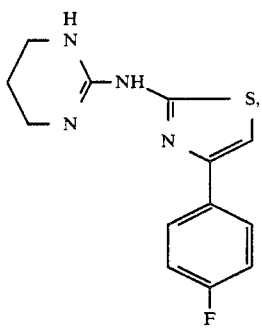

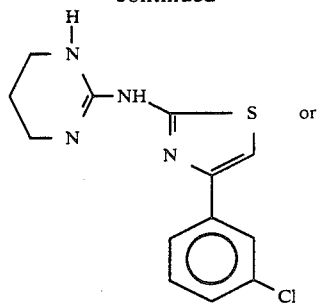

(25)

2. A pharmaceutical composition useful for combating mycoses comprising a 2-aminothiazole according to claim 1 and a pharmaceutically acceptable excipient therefor.

3. A method for combating mycoses comprising administering to a patient in need of such treatment an effective amount of a 2-aminothiazole according to claim 1.

4. A method of combating mycoses in warm blood animals comprising administering to said animal an antimycotically effective amount of a 2-aminothiazole according to claim 1, either alone or in admixture with an inert excipient or in the form of a medicament.

5. A medicament in dosage unit form comprising an antimycotically effective amount of a 2-aminothiazole according to claim 1 either alone or in admixture with a suitable pharmaceutical excipient.

* * * * *

UNITED STATES PATENT AND TRADEMARK OFFICE
CERTIFICATE OF CORRECTION

PATENT NO. : 5,104,879

DATED : April 14, 1992

INVENTOR(S) : Ippen et al.

It is certified that error appears in the above-identified patent and that said Letters Patent is hereby corrected as shown below:

Col. 52, line 40  Delete " blood " and substitute -- blooded --

Signed and Sealed this

Second Day of November, 1993

Attest:

BRUCE LEHMAN

*Attesting Officer*   *Commissioner of Patents and Trademarks*